United States Patent [19]
Chen et al.

[11] Patent Number: 6,092,531
[45] Date of Patent: Jul. 25, 2000

[54] MOVABLE MAGNET TRANSMITTER FOR INDUCING ELECTRICAL CURRENT IN AN IMPLANTED COIL

[75] Inventors: James C. Chen, Bellevue; David J. Brown; Darrin Huston, both of Enumclaw; Brian D. Wilkerson, Issaquah, all of Wash.

[73] Assignee: Light Sciences Limited Partnership, Issaquah, Wash.

[21] Appl. No.: 09/325,022

[22] Filed: Jun. 3, 1999

Related U.S. Application Data

[62] Division of application No. 09/021,693, Feb. 10, 1998.

[51] Int. Cl.[7] .......................... A61M 37/00; H02K 33/00
[52] U.S. Cl. .................. 128/899; 310/171; 600/9; 600/13; 607/65; 607/33
[58] Field of Search ................. 310/171, 50, 46, 310/40 R; 128/899; 600/9, 13; 607/2, 33, 32, 61, 65

[56] References Cited

U.S. PATENT DOCUMENTS

| | | | |
|---|---|---|---|
| 2,481,196 | 9/1949 | Bulliet | 310/80 |
| 3,668,448 | 6/1972 | Hayasaka | 310/166 |
| 3,672,352 | 6/1972 | Summers | 128/2 R |
| 3,836,289 | 9/1974 | Wolford et al. | 417/415 |
| 3,942,535 | 3/1976 | Schulman | 128/419 PS |
| 3,967,146 | 6/1976 | Howard | 310/80 |
| 4,005,346 | 1/1977 | Hsia | 318/128 |
| 4,038,572 | 7/1977 | Hanagan | 310/46 |
| 4,038,625 | 7/1977 | Tompkins et al. | 336/83 |
| 4,163,164 | 7/1979 | Pieters | 310/103 |
| 4,338,951 | 7/1982 | Saliga | 128/695 |
| 4,392,071 | 7/1983 | Gauthier | 310/113 |
| 4,432,363 | 2/1984 | Kakegawa | 128/419 PS |
| 4,443,776 | 4/1984 | Cunningham | 335/302 |
| 4,461,302 | 7/1984 | Philipps et al. | 128/630 |
| 4,507,048 | 3/1985 | Belenger et al. | 415/90 |
| 4,564,778 | 1/1986 | Yoshida | 310/177 |
| 4,665,896 | 5/1987 | LaForge et al. | 128/1 D |
| 4,679,560 | 7/1987 | Galbraith | 128/419 R |
| 4,736,732 | 4/1988 | Munck et al. | 128/798 |
| 4,741,339 | 5/1988 | Harrison et al. | 128/419 R |
| 4,831,299 | 5/1989 | Hayasaka | 310/166 |
| 4,927,337 | 5/1990 | Lustwerk | 417/420 |
| 5,109,843 | 5/1992 | Melvin et al. | 128/419 R |
| 5,112,200 | 5/1992 | Isaacson et al. | 417/356 |
| 5,146,123 | 9/1992 | Yarr | 310/15 |
| 5,314,457 | 5/1994 | Jeutter et al. | 607/116 |
| 5,350,413 | 9/1994 | Miller | 607/61 |
| 5,569,156 | 10/1996 | Mussivand | 600/16 |
| 5,945,762 | 8/1999 | Chen et al. | 310/171 |

OTHER PUBLICATIONS

Hilton, Edgar F., et al. "Magnetic Suspension Controls for a New Continuous Flow Ventricular Assist Device." ASAIO Journal. 1977. 43:M598–M603.

Kono, Satoshi, et al. "In Vivo and In Vitro Evaluation of the pulsatile Mode of a Magnetically Suspended Centrifugal Pump." ASAIO Journal. 1977. 43:M580–M584.

Xu, Longya, et al. Analysis of a New PM Motor Design for a Rotary Dynamic Blood Pump. ASAIO Journal. 1997. 43:M559–M564.

Yamane, Takashi, et al. "Fluid Dynamic Characteristics of Monopivot Magnetic Suspension Blood Pumps." ASAIO Journal. 1997. 43:M635–M638.

*Primary Examiner*—Elvin Enad
*Assistant Examiner*—Burton S. Mullins
*Attorney, Agent, or Firm*—Ronald M. Anderson

[57] ABSTRACT

An external power head is energized by a motor causing movement of an element that produces a varying magnetic field, thereby inducing power in an implanted receiver coil within a patient's body. The external power head includes either one or more moving permanent magnets, or one or more moving elements that vary the magnetic flux coupled to the implanted receiver coil. As a result of the varying magnetic field experienced by the implanted receiver coil, an electric current flows from the implanted receiver coil to energize an implanted medical device.

15 Claims, 11 Drawing Sheets

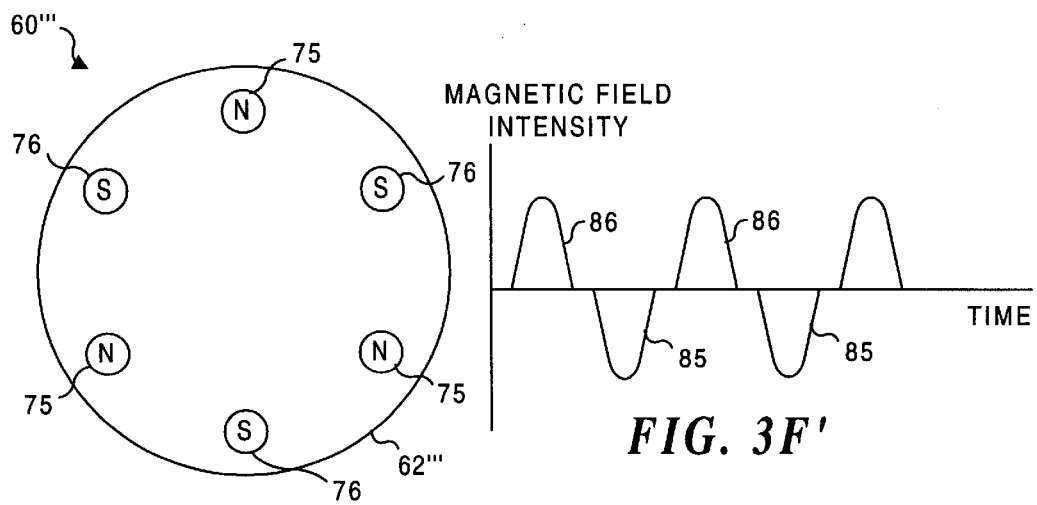
FIG. 3F
FIG. 3F'
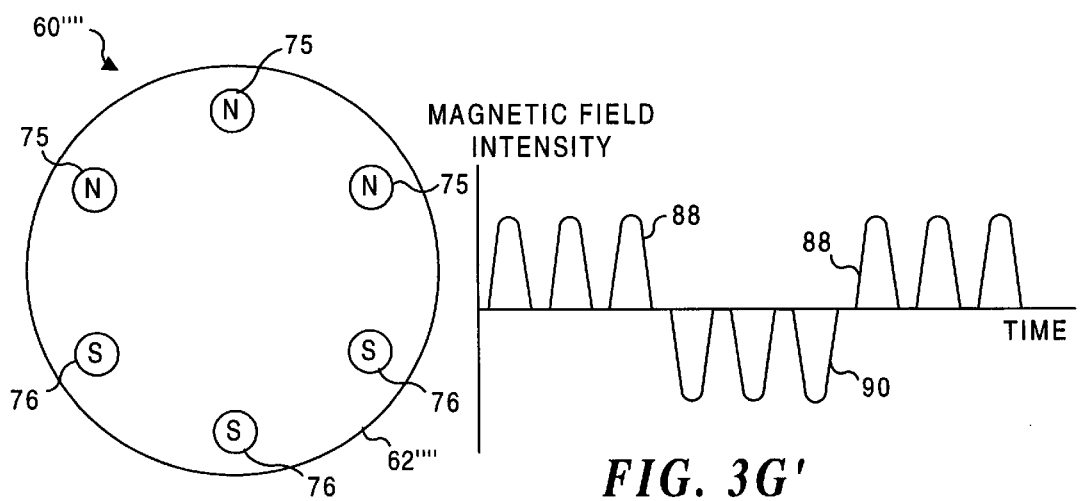
FIG. 3G
FIG. 3G'
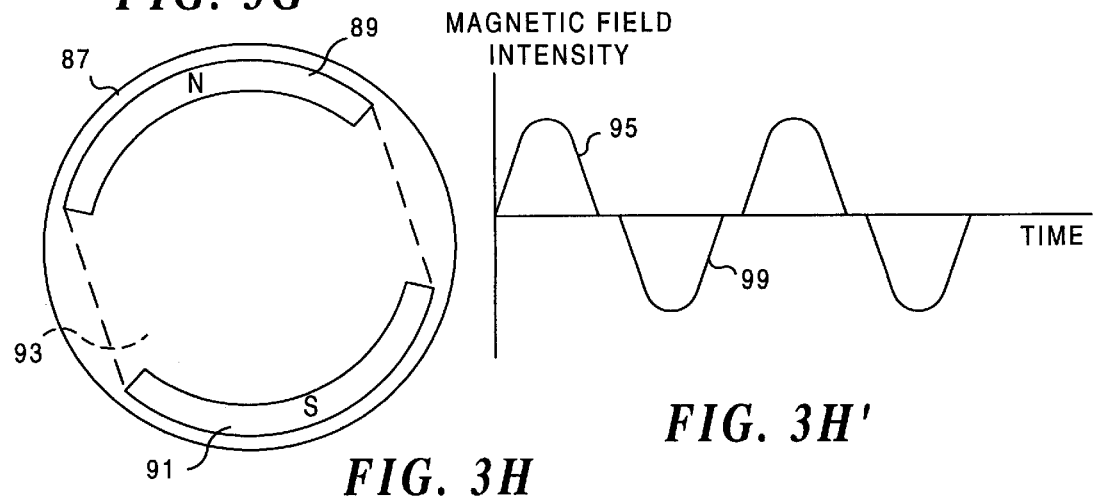
FIG. 3H
FIG. 3H'

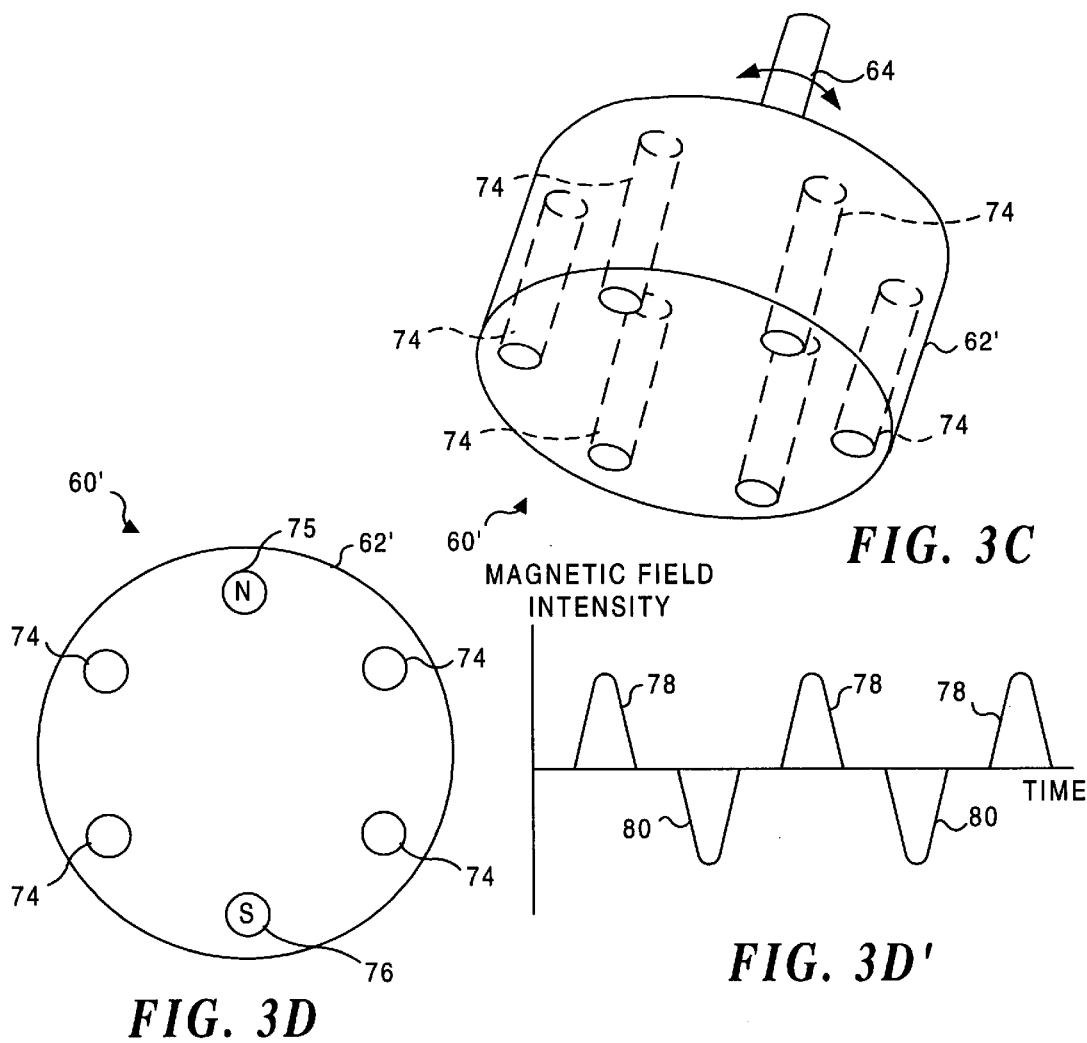
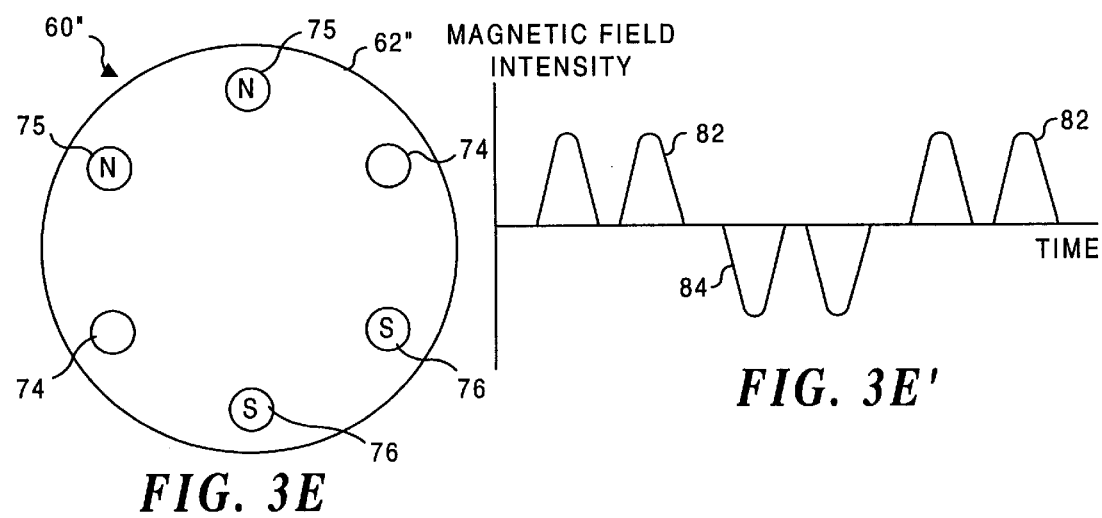
FIG. 3E
FIG. 3E'

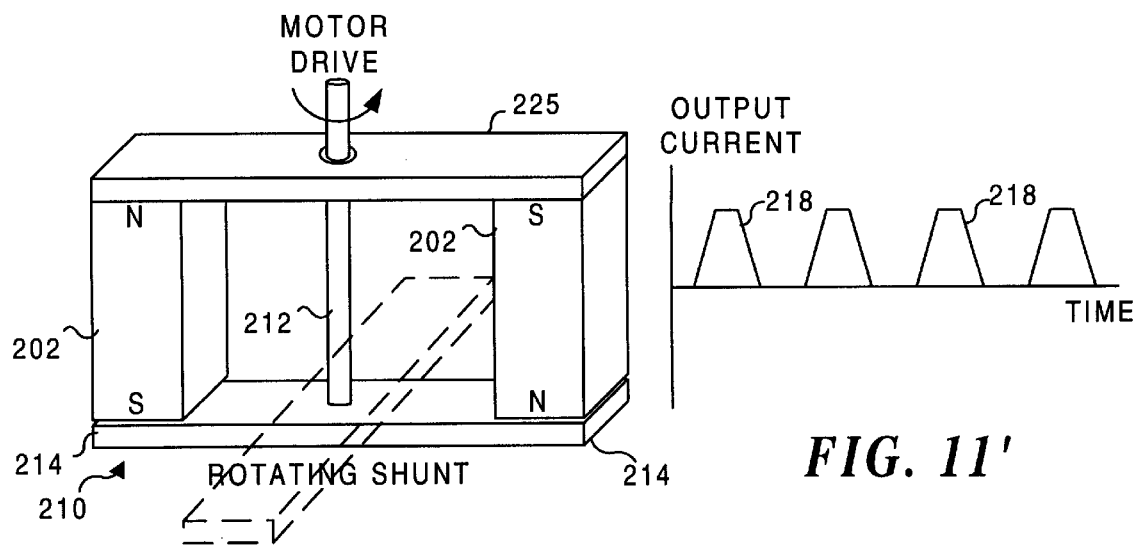
FIG. 11
FIG. 11'
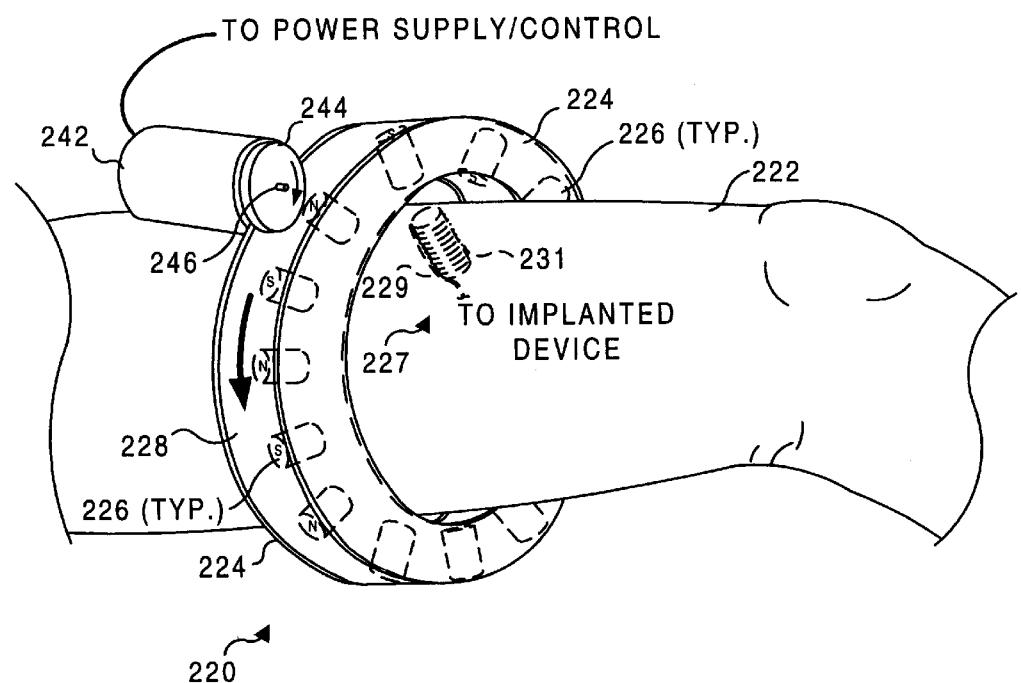
FIG. 12

MOVABLE MAGNET TRANSMITTER FOR INDUCING ELECTRICAL CURRENT IN AN IMPLANTED COIL

This application is a divisional application, based on prior copending application Ser. No. 09/021,693, filed on Feb. 10, 1998, the benefit of the filing date of which is hereby claimed under 35 U.S.C. § 120.

FIELD OF THE INVENTION

The present invention generally pertains to supplying energy to an electrical circuit within a patient's body from an external source, and more specifically, to inducing an electrical current to flow in an implanted coil within the patient's body using magnetic energy supplied from outside the body.

BACKGROUND OF THE INVENTION

Various types of medical devices such as cochlear implants, artificial hearts, and neural stimulators have been developed that are designed to be surgically inserted within a patient's body to carry out a medically related function for an extended period of time. Although a power lead connected to the implanted device and extending outside the patient's body can be used to supply electrical power required to energize the device, any lead that passes through the skin increases the risk of infection if left in place for more than a few days. To avoid this problem, power can be supplied to an implanted medical device from an internal battery pack. However, any battery used for extended periods of time will eventually need to either be recharged or replaced. Replacing an internally implanted battery subjects the patient to further invasive surgery and is thus not desirable. Recharging a battery through directly connected leads again creates a risk of infection.

A solution to this problem is to recharge the battery by transcutaneously coupling power from an external source to an implanted receiver coil that is connected to the battery. In the prior art, an external transmitter coil is typically energized with an alternating current (AC), producing either a radio frequency (RF) signal or a varying magnetic flux that passes through the patient's skin and excites an implanted receiving coil. The electrical current that flows in the implanted receiving coil because of the RF signal that is received or as a result of the magnetic induction can be rectified and filtered for use in providing direct current (DC) power to the implanted device or in charging a battery pack that provides power to the implanted device. Alternatively, electrical current from the implanted coil may be directly applied to power the implanted medical device if the device will operate on AC at the frequency of the transmitted power. It should be noted that the implanted receiving coil and any related electronic circuitry for filtering and/or regulating the electrical current may be located at a different point in the patient's body from that at which the implanted medical device is disposed. The implanted medical device may be connected to the receiving coil and any associated electronic circuitry through a lead that passes through the patient's body between the two sites.

To provide sufficient power to energize an implanted medical device or recharge its battery, it may be necessary to energize the external transmitter coil with a relatively high current. The current flowing through the external transmitter coil and the power dissipated in the resistance of the coil can be sufficiently high to cause overheating of the external coil unless it is cooled using fans or some other cooling mechanism. Also, a potential shock hazard may exist, since several hundred volts may be applied to properly energize the external transmitter coil. Even if the housing of the external coil is adequately cooled by including one or more fans to move air through the housing, the heat generated in the transmitter that is carried by the fan driven air How may blow over the patient's body and can cause the patient to feel uncomfortably warm.

Thus, it would clearly be preferable to provide an external transmitter that does not require cooling and which need not be energized with a substantial electrical current to induce the current required in an implanted coil. It would also be preferable if the external transmitter is relatively simple, more compact in size, lighter in weight, and lower in cost than conventional electromagnetic coil transmitters. It would also be desirable to provide a relatively simple mechanism for selectively adjusting the power delivered to an implanted coil from such an external transmitter.

SUMMARY OF THE INVENTION

In accord with the present invention, an external transmitter is defined that is adapted for magnetically exciting an implanted receiver coil by causing an electrical current to flow in the implanted receiver coil. The external transmitter includes a support and a magnetic field generator that is rotatably mounted to the support. A prime mover is drivingly coupled to the magnetic field generator to cause an element of the magnetic field generator to move relative to the support. Movement of the element produces a varying magnetic field that is adapted to induce an electrical current to flow in the implanted receiver coil.

The external transmitter also preferably includes a housing that substantially encloses the support and the magnetic field generator, and the prime mover preferably comprises an electric motor. In one form of the invention, the prime mover is disposed within the housing. Alternatively, the prime mover is disposed remote from the magnetic field generator and is coupled to the magnetic field generator through a drive shaft.

Further, the magnetic field generator comprises a permanent magnet, preferably fabricated of a rare earth alloy. In one or more configurations of the invention, the element moved by the prime mover comprises the permanent magnet, which is rotated about an axis. Rotation of the permanent magnet varies a magnetic flux along a path that includes the implanted receiver coil. Increasing a speed at which the permanent magnet is rotated (or otherwise moved) increases a magnitude of the electrical current induced in the implanted receiver coil.

In another embodiment, the permanent magnet is oscillated back and forth relative to an axis of the permanent magnet. Oscillation of the permanent magnet varies a magnetic flux along a path that includes the implanted receiver coil.

A flux linkage bar comprising a material that enhances magnetic flux linkage is preferably disposed adjacent a magnetic pole of the permanent magnet. The flux linkage bar couples magnetic flux from a pole of the permanent magnet into a path that couples with the implanted receiver coil, enabling the permanent magnet to be displaced from the implanted receiver coil and thereby minimizing torque applied to the implanted receiver coil by the permanent magnet.

The magnetic field generator preferably comprises a plurality of permanent magnets. An adjustment member is included to selectively vary a maximum magnetic flux produced by the magnetic field generator for coupling with the implanted receiver coil. The adjustment member varies the position of the plurality of permanent magnets relative to the support. In one embodiment, the permanent magnets include a "driven" permanent magnet that is moved by the prime mover, and a "follower" permanent magnet that is magnetically coupled to the driven permanent magnet and is moved by its motion.

In another embodiment, the permanent magnets are fixed relative to the support. In this case, the moving element comprises a flux shunt member that is moved by the prime mover to intermittently pass adjacent pole faces of the plurality of permanent magnets so as to intermittently provide a magnetic flux linkage path between the pole faces that effectively shunts the magnetic flux. When the magnetic flux is thus shunted, substantially much less magnetic flux couples to the implanted receiver coil. The shunting of the magnetic flux through the moving element substantially "shuts off" the magnetic field produced by the permanent magnets that would otherwise be experienced outside the housing. The embodiments that employ fixed permanent magnets are generally less efficient in inducing an electrical current in the implanted receiver coil than those in which a permanent magnet is moved relative to the implanted receiver coil.

A plurality of turns of a conductor can be wound around the magnetic field generator to selectively vary the magnetic field that it produces. The plurality of turns of the conductor are adapted to connect to a source of an electrical current, producing a magnetic field that either opposes or aids the magnetic field produced by the magnetic field generator, thereby varying the magnetic field experienced by the receiver coil.

In yet another embodiment, the permanent magnets are radially movable relative to an axis of a shaft that couples to the prime mover. The permanent magnets are attracted to each other when the shaft is at rest, but an actuator moves the permanent magnets away from each other to improve the coupling of the magnetic flux that they produce with the implanted receiver coil when the shaft is rotating. The disposition of the permanent magnets adjacent to each other when the shaft begins to rotate reduces the startup torque required to rotate the shaft. Furthermore, by controlling the radial disposition of the permanent magnets, it is possible to control a magnitude of the electrical current induced in the implanted receiver coil.

Another aspect of the present invention is directed to a method for generating a varying magnetic field to couple energy to an implanted receiver coil. The steps of this method are generally consistent with the functions provided by the elements of the apparatus discussed above.

BRIEF DESCRIPTION OF THE DRAWING FIGURES

The foregoing aspects and many of the attendant advantages of this invention will become more readily appreciated as the same becomes better understood by reference to the following detailed description, when taken in conjunction with the accompanying drawings, wherein:

FIG. 3C is a perspective bottom view of a driven disk for the power head, for use as a test prototype;

Figure 4A:
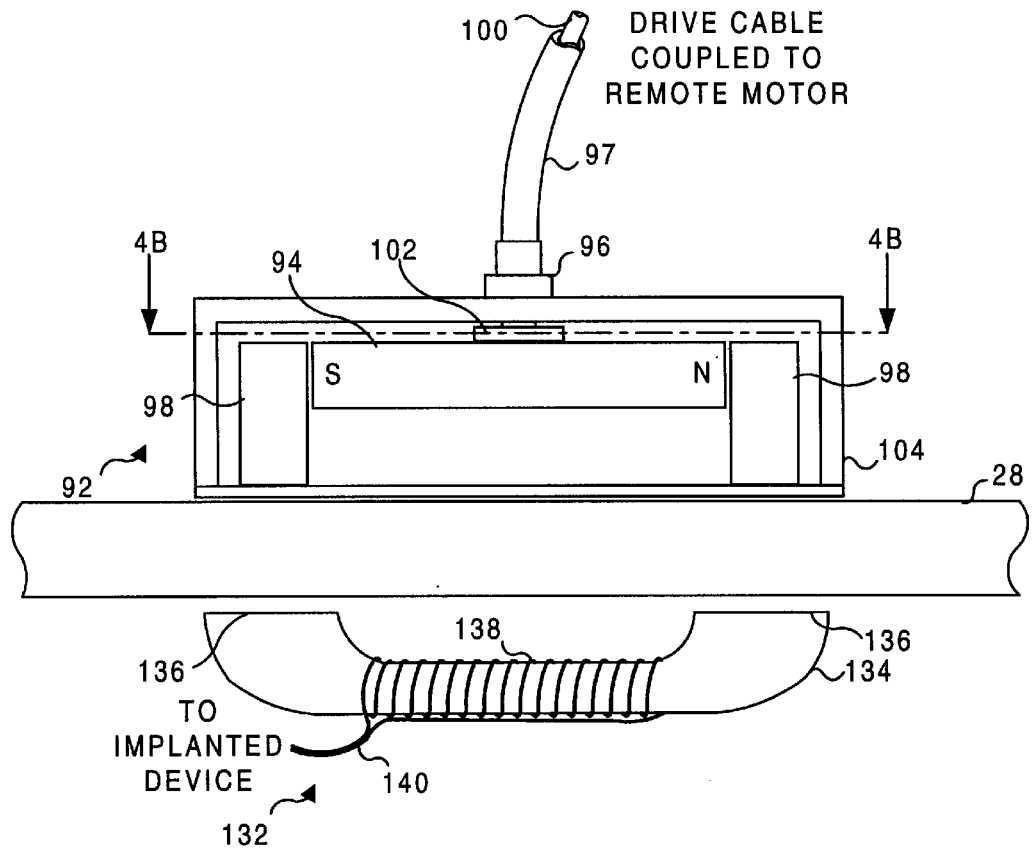
Figure 4B:
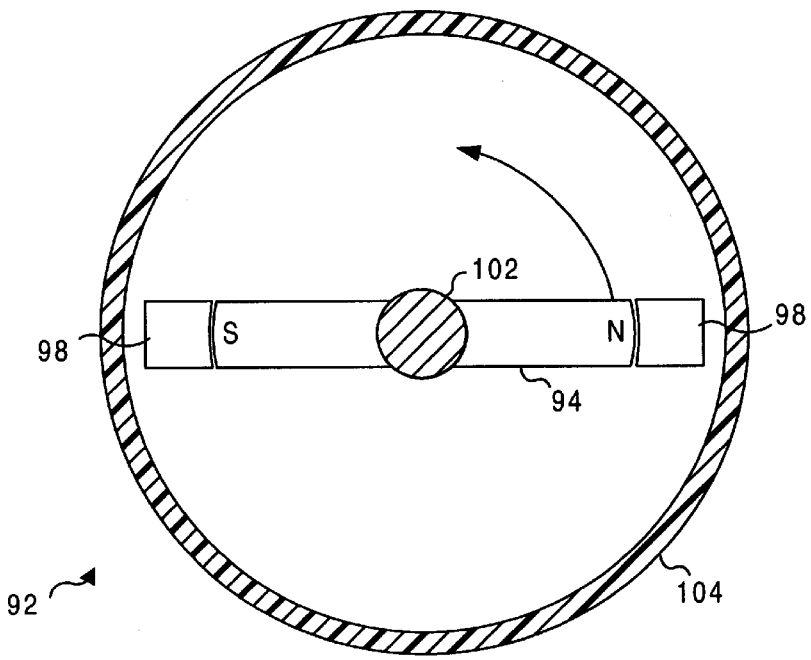
Figure 5:
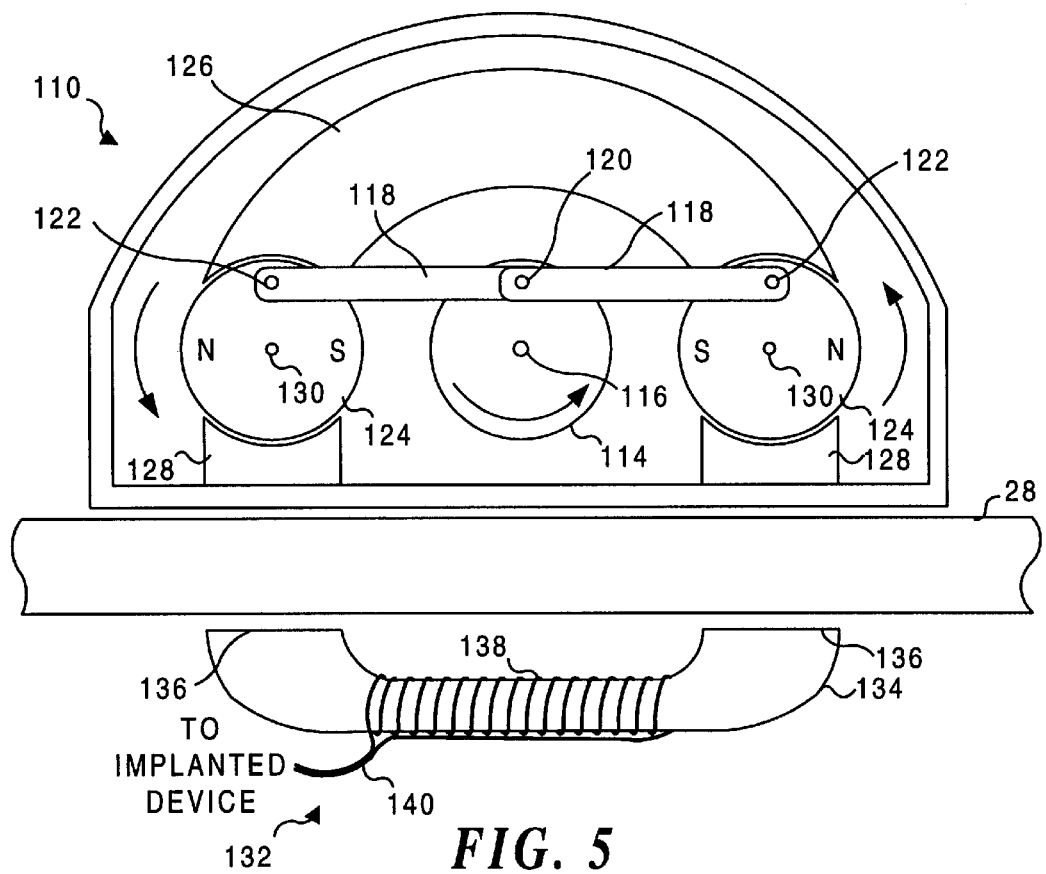
Figure 6A:
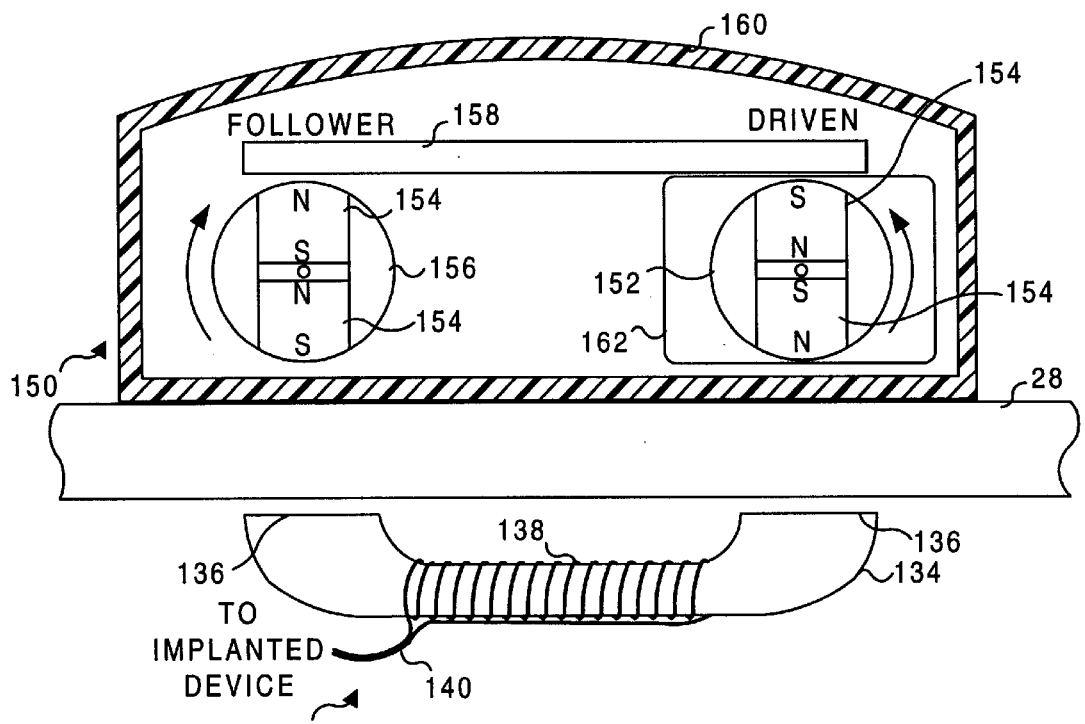
Figure 6B:
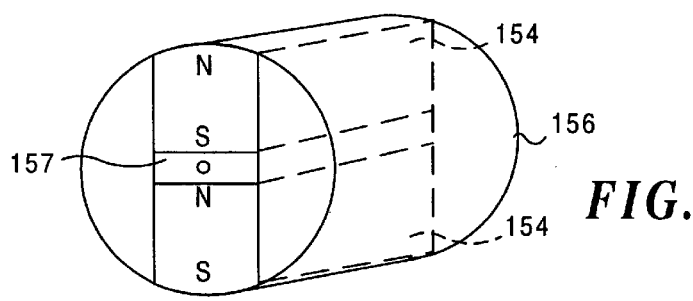
Figure 7:
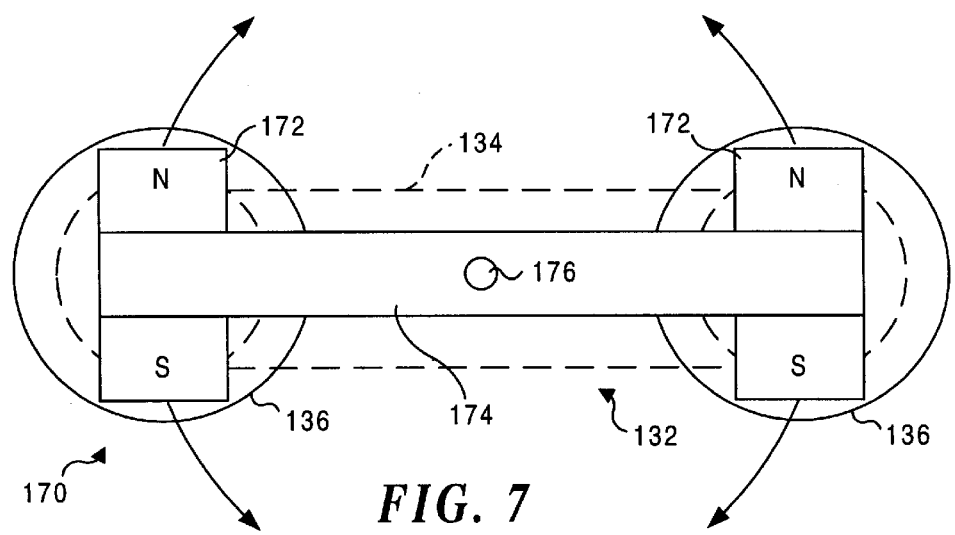
Figure 8:
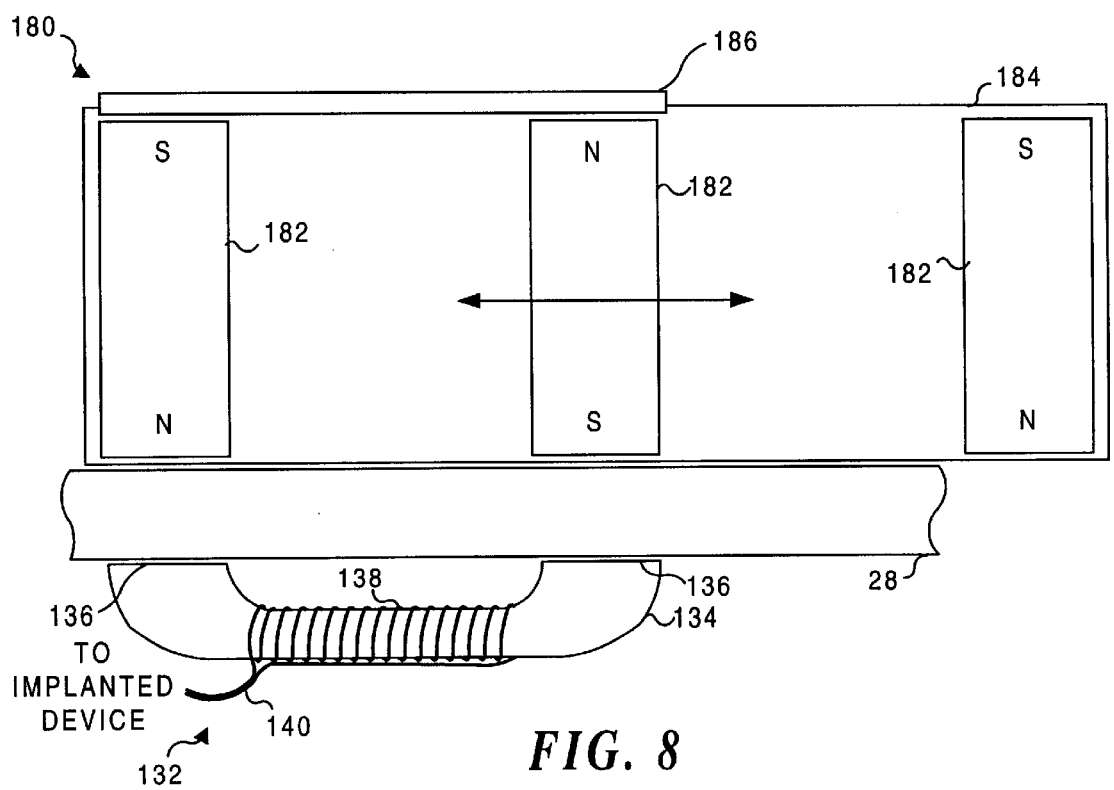
Figure 9:
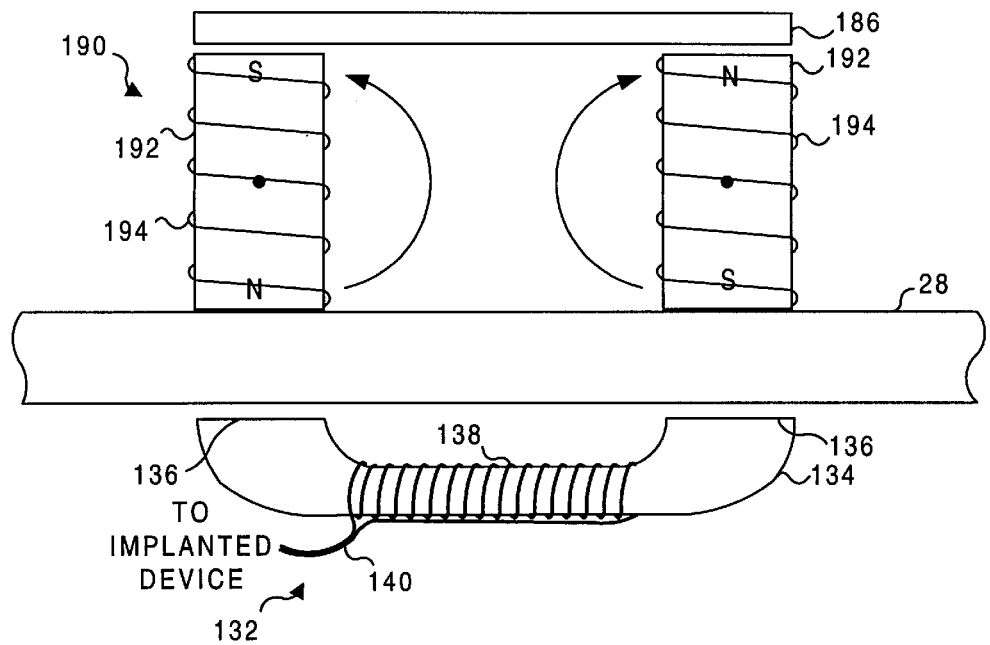
Figure 10:
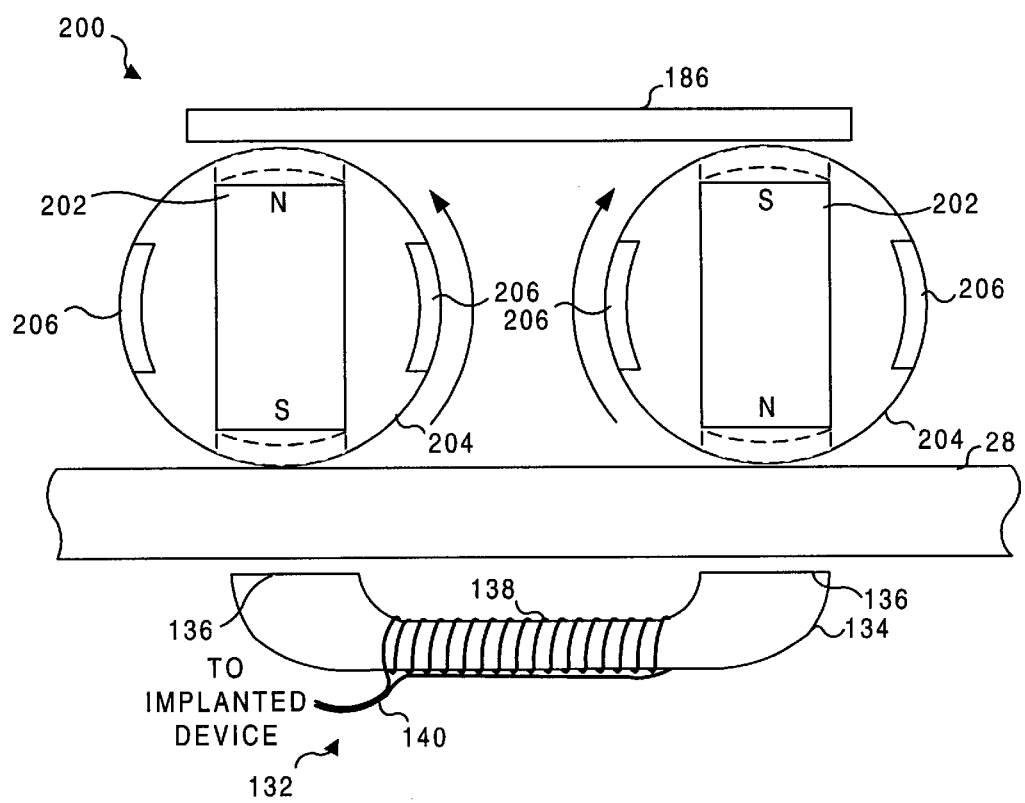
Figure 13:
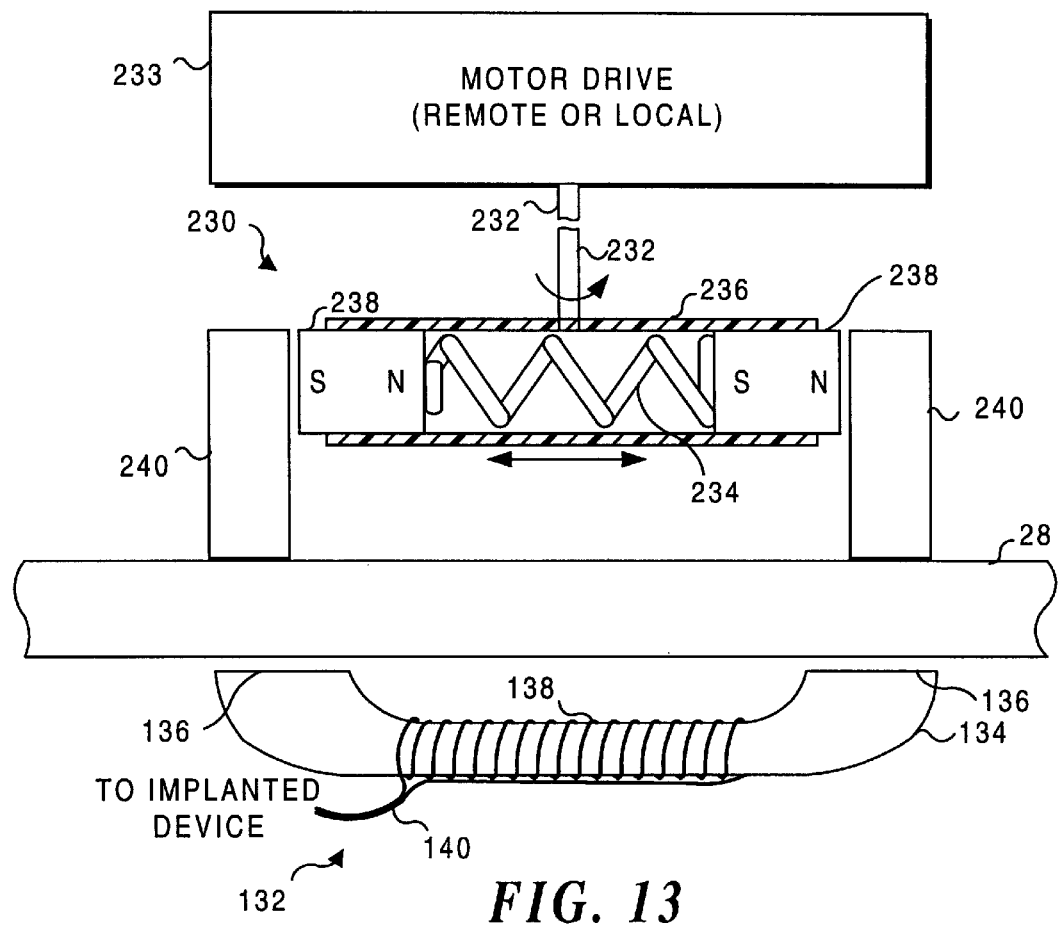
Figure 14A:
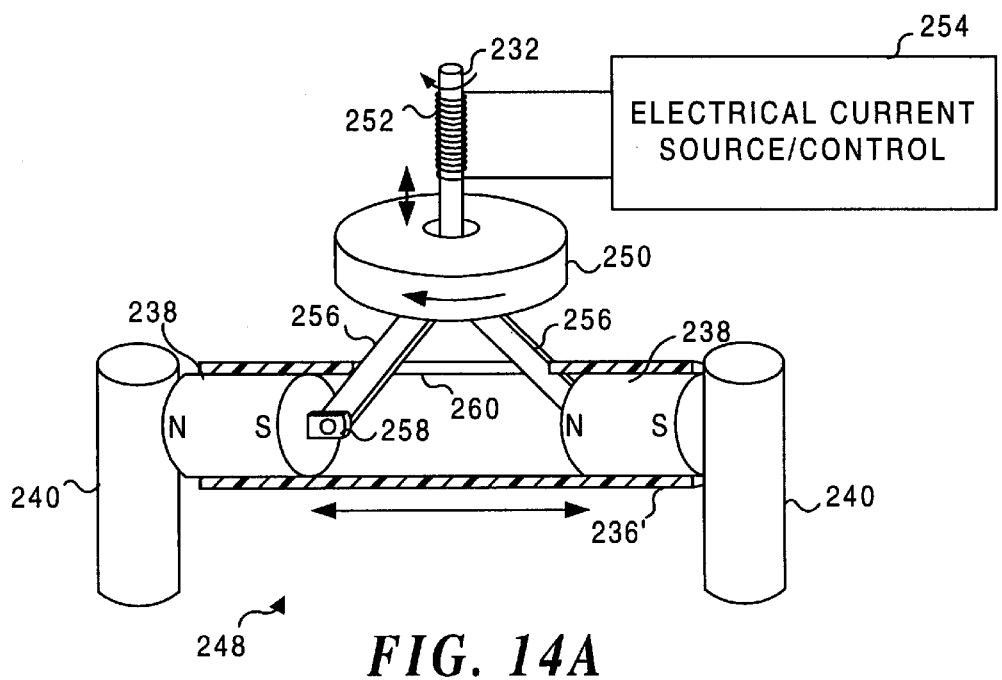
Figure 14B:
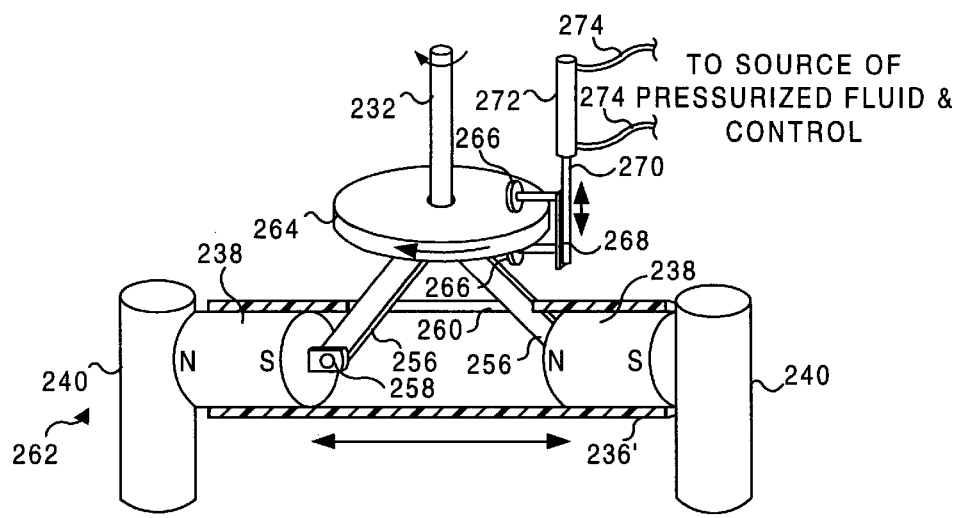
Figure 15:
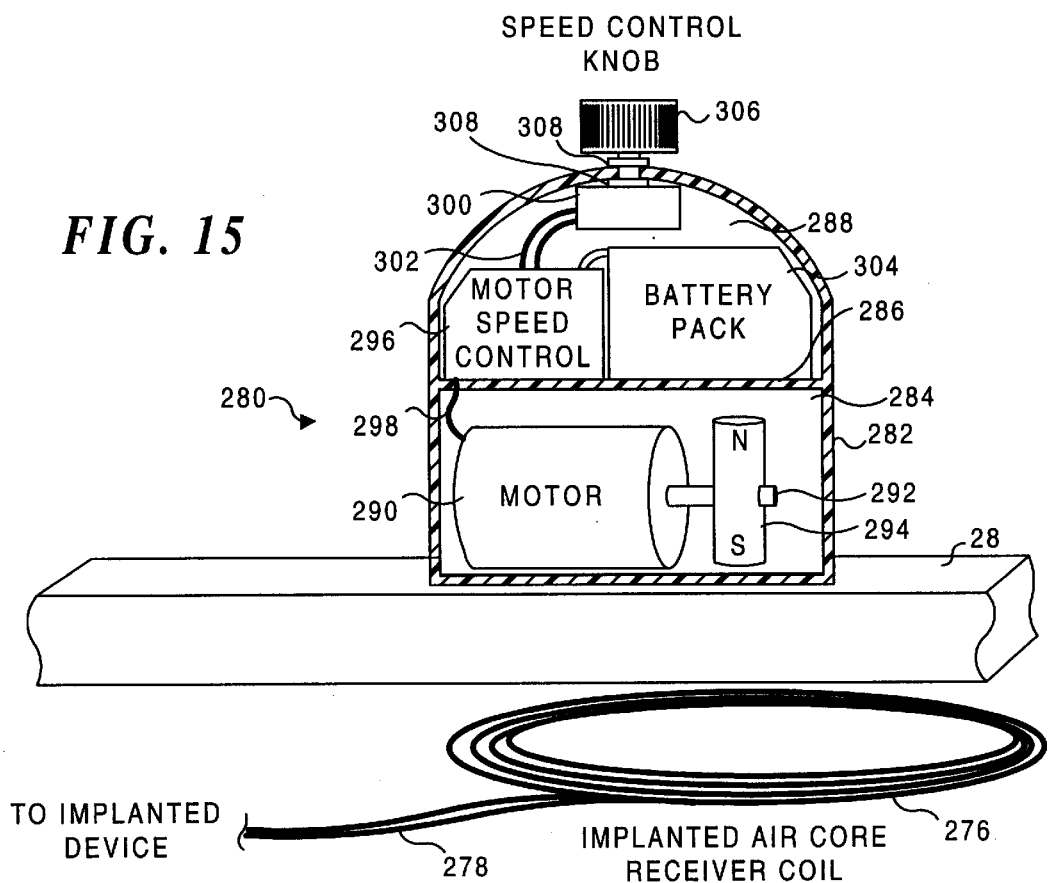

FIGS. 3D and 3D' are respectively a bottom view of the driven disk, with two permanent magnets, and a graph of related magnetic field intensity waveforms vs. time;

FIGS. 3E and 3E' are respectively a bottom view of the driven disk, with four permanent magnets, and a graph of related magnetic field intensity waveforms vs. time;

FIGS. 3F and 3F' are respectively a bottom view of the driven disk, with six alternating pole permanent magnets, and a graph of related magnetic field intensity waveforms vs. time;

FIGS. 3G and 3G' are respectively a bottom view of the driven disk, with six permanent magnets in an arrangement with three consecutive south pole faces and three consecutive north pole faces on the bottom of the drive disk, and a graph of related magnetic field intensity waveforms vs. time;

FIGS. 3H and 3H' are respectively a bottom view of a driven disk including a pair of arcuate shaped permanent magnets, and a graph of related magnetic field intensity waveforms vs. time;

FIGS. 4A and 4B are respectively a side elevational cross-sectional view of another embodiment of an external power head coupled to a receiver coil in which a rotating permanent magnet produces a magnetic flux that is coupled to the receiver coil by two flux linkage bars, and a cross-sectional view of the external power head taken along section lines 4B—4B in FIG. 4A;

FIG. 5 is a cross-sectional side elevational view of another embodiment of the power head and the receiver coil, in which a drive wheel rotates two permanent magnets;

FIGS. 6A and 6B are respectively a cross-sectional view of yet another embodiment of the power head and the receiver coil in which one permanent magnet is directly driven to rotate and another permanent magnet magnetically follows the rotation of the driven permanent magnet, and an enlarged view of the following permanent magnet;

FIG. 7 is a plan view of an external power head (housing not shown) in which two permanent magnets are driven to reciprocate back and forth above the implanted receiver coil;

FIG. 8 is a side elevational view of an external power head (housing not shown) in which three permanent magnets are driven to linearly reciprocate above the implanted receiver coil;

FIG. 9 is a side elevational view of an external power head (housing not shown) in which conductors coiled around two permanent magnets selectively vary a magnetic field produced by the permanent magnets;

FIG. 10 is a side elevational view of an external power head (housing not shown) in which two rotating flux linkage tabs vary the magnetic flux linked from two fixed permanent magnets to the implanted receiver coil;

FIGS. 11 and 11' are respectively a perspective view of an external power head (housing not shown) in which fixed permanent magnets and a rotating flux shunt bar are provided, and a graph of the current pulses vs. time produced in the implanted receiver coil;

FIG. 12 is a perspective view of an external ring power head in which a plurality of permanent magnets are driven past an implanted receiver coil that is implanted in a patient's leg;

FIG. 13 is a side elevational view of the implanted receiver coil and an external power head (housing not shown) in which two permanent magnets are slidably supported within a rotating tube so as to minimize starting torque, and so as to reduce an external magnetic field (outside the housing) when the permanent magnets are not rotating;

FIGS. 14A and 14B are external power heads in which a force is applied by a solenoid coil/ring magnet, and by a fluid cylinder, respectively, to two permanent magnets that are slidably mounted in a rotating tube so as to minimize starting torque, and so as to reduce an external magnetic field (outside the housing) when the permanent magnets are not rotating; and FIG. 15 is a cut-away side elevational view of yet another power head including a speed control and a permanent magnet that is drivingly rotated within a plane, which is generally transverse to the plane of an internal air core receiver coil disposed within a patient's body.

DESCRIPTION OF THE PREFERRED EMBODIMENTS

Figure 1:
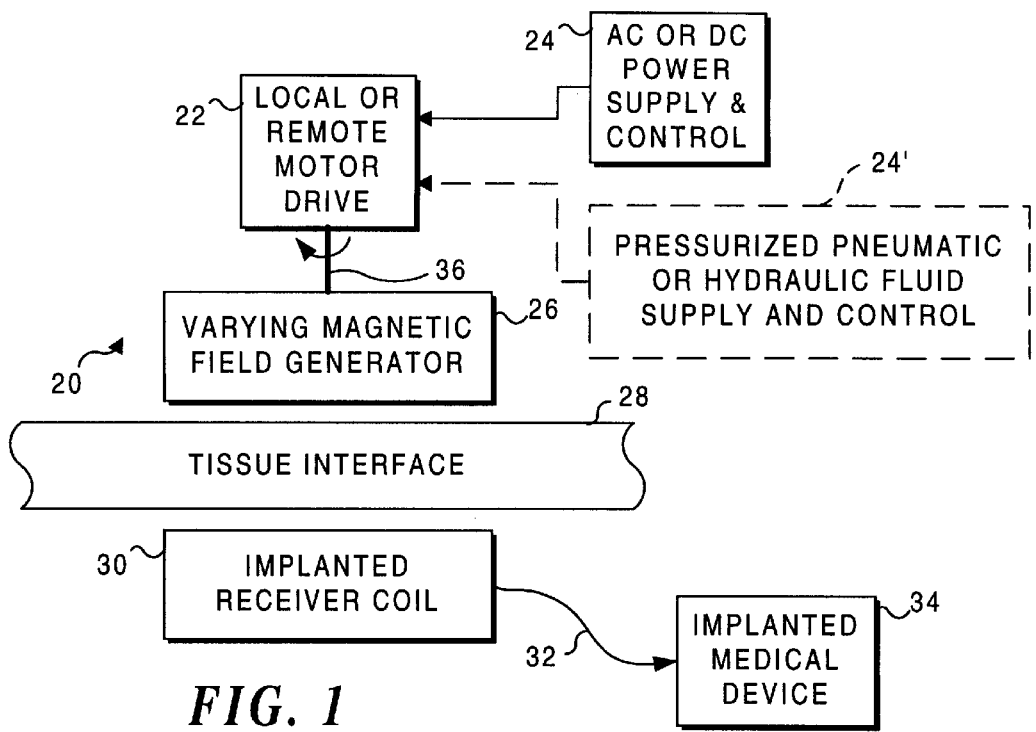
FIG. 1 is a block diagram illustrating the use of the present invention for energizing an implanted medical device within a patient's body.

With reference to FIG. 1, a block diagram shown therein illustrates a typical application of the present invention. In this application, an external power head 20 includes a local (or remote) motor drive 22 that is energized from a power supply/control 24. While the motor is preferably electrical, it is also contemplated that a pneumatic or hydraulic motor can alternatively be used as the prime mover. A pressurized pneumatic or hydraulic fluid supply and control 24' is shown for use in controlling such a motor. By using a fluid drive motor, electrical current to and in the device is eliminated, which may be desirable in certain applications. However, an electrically powered motor is typically lower in cost and generally preferable. To provide electrical current to operate an electrical motor, power supply/control 24 preferably comprises a DC battery supply; alternatively the power supply can be energized by connection to an AC line source (not separately shown). If a DC battery supply is used, the batteries may be of the rechargeable type, e.g., nickel-cadmium, or nickel-hydride.

Local (or remote) motor drive 22 comprises a prime mover that supplies a mechanical driving force to actuate a varying magnetic field generator 26. If the mechanical driving force is provided locally, the motor drive is coupled to the varying magnetic field generator through a drive shaft 36. Conversely, if the drive is disposed at a remote point, separate from the varying magnetic field generator, the mechanical drive force can be provided through a flexible cable (not separately shown) that extends between the remote motor drive and varying magnetic field generator 26. The movement provided by the motor causes a variation in the magnetic field produced by magnetic field generator that changes the magnetic flux through a path outside of external power head 20.

External power head 20 is intended to produce a varying magnetic field that induces a corresponding electrical current to flow in a conductor that is sufficiently close to the external power head to permit magnetic coupling with the conductor to occur. In one preferred application of the external power head, the varying magnetic field it produces passes through a tissue interface 28 and couples with an implanted receiver coil 30 that is positioned inside the body of a patient (not shown), just inside tissue interface 28 and directly opposite varying magnetic field generator 26. Tissue interface 28 may comprise, for example, the dermal layer of the patient's body. The typical separation between varying magnetic field generator 26 and implanted receiver coil 30 may vary from about 0.5 cm to about 2.0 cm.

The receiver coil can be implanted between bony structures such as under the dermal layer, adjacent to a patient's ribs, on the chest. Flanges (not shown) extending from the periphery of the implanted receiver coil can be fastened to the ribs using bone screws designed to affix devices to a bone in which the screws are installed and to resist working out of the bone. However, it should be noted that the implanted receiver coil need not be coupled to any supporting bone structure or even mounted proximate to a bone structure. But, by supporting the receiver coil between or just below the ribs and immediately beneath the dermal layer (or by optionally attaching the implanted receiver coil to any suitable bony structure in the patient's body), the device will be maintained in a desired position for optimal power transfer. Implanted receiver coil 30 is connected to an implanted medical device 34 through a lead 32, which conveys the electrical current induced in the implanted receiver coil by the varying magnetic field; this electrical current energizes the implanted medical device.

Implanted medical device 34 may comprise, for example, an implanted light source for administering photodynamic therapy (PDT). However, it is not intended that the present invention be in any way limited to energizing such a device, since many other types of implanted medical devices can be energized using the present invention. The implanted medical device may include a storage battery or storage capacitor for storing energy coupled to the implanted receiver coil 30. Alternatively, a battery or capacitor for storing energy (neither shown) may be disposed at the implanted receiver coil. It will also be apparent that the medical device can be directly energized using the present invention, in which case, an energy storage device need not be provided.

Figure 2:
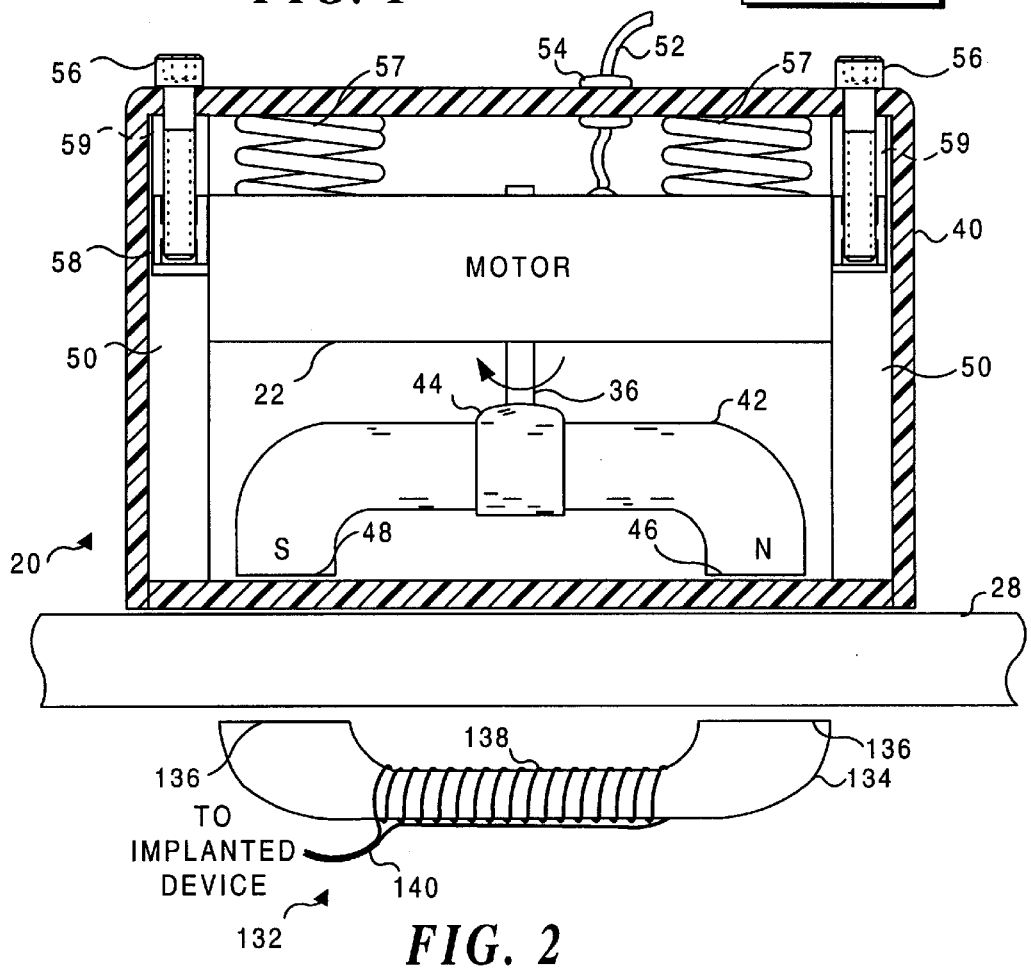
FIG. 2 is a cross-sectional view of a first embodiment of an external power head for coupling a varying electromagnetic flux into a implanted receiver coil, in accord with the present invention.

FIG. 2 illustrates a first embodiment of external power head 20 in which motor drive 22 is disposed within a housing 40 of the external power head. Motor drive 22 is coupled to a generally C-shaped permanent magnet 42 through rotating drive shaft 36. The rotating drive shaft connects to a collar 44 around the midsection of permanent magnet 42. Preferably in this and in each of the other embodiments of the present invention described below, the permanent magnet is formed of a neodymium-iron-boron alloy or other rare earth or metal alloy that produces a relatively high magnetic flux density. Other types of ferromagnetic alloys are also acceptable for this purpose, although it is generally desirable to use a material for the permanent magnets that produces a relatively strong magnetic field in the present invention. Permanent magnet 42 includes a north pole face 46 and a south pole face 48 that face downwardly and are disposed immediately adjacent the interior side of the lower surface of housing 40. To prevent undesired shunting of the magnetic flux between north pole face 46 and south pole face 48 and eddy current losses that would occur if a conductive material were used, housing 40 preferably comprises a plastic polymer material that is a good electrical insulator and does not block the magnetic flux produced by the permanent magnet.

Four vertical support bars 50 arc disposed inside housing 40, one adjacent each corner. Threaded tabs extend outwardly from each end of motor drive 22, into slots 59 that are formed within vertical support bars 50. Tabs 58 slide within slots 59 as set screws 56 at each corner of the top of housing 40 are threaded into or out of the tabs, thereby enabling the vertical elevation of motor drive 22, and thus the vertical position of the permanent magnet, to be adjusted within housing 40. As set screws 56 are threaded further into tabs 58, motor drive 22 is drawn upwardly, elevating permanent magnet 42 away from the bottom of housing 40 and reducing the magnetic flux coupled to an implanted receiver coil 132. The electrical current induced in implanted receiver coil 132 can be controlled by thus adjusting the vertical position of motor drive 22 and permanent magnet 42 within housing 40 or by changing the separation between the housing and the implanted receiver coil. Other techniques for adjusting the magnitude of the electrical current induced in implanted receiver coil 132, such as by varying the rotational speed of the permanent magnet, are discussed below.

Figure 3A:
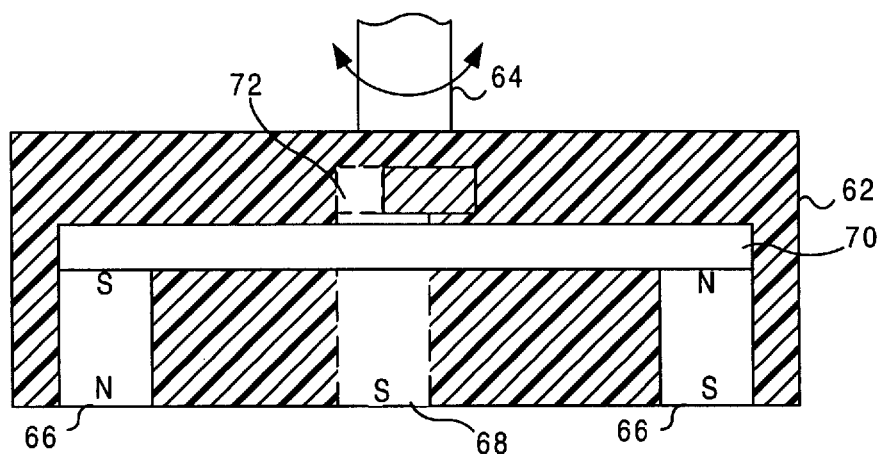
FIGS. 3A and 3B illustrate a cross-sectional elevational view and a bottom view of a second embodiment of an external power head that includes two sets of permanent magnets.
Figure 3B:
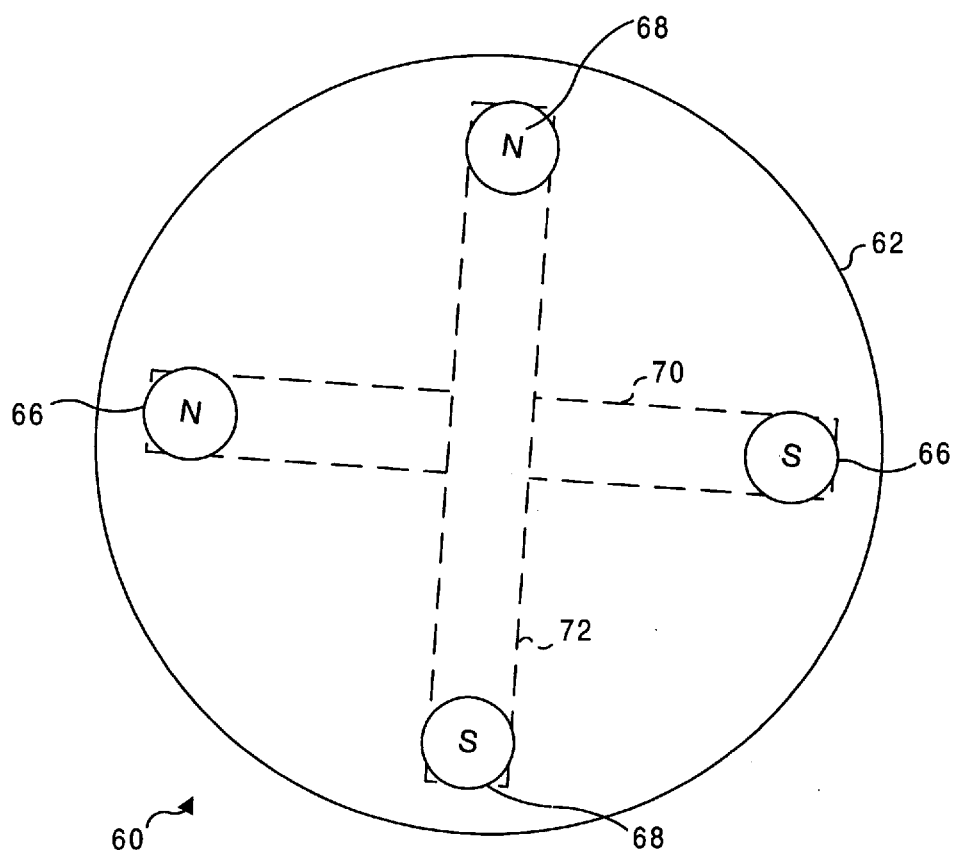

FIGS. 3A and 3B show an alternative embodiment, illustrating a varying magnetic field generator 60. In these Figures, the housing and motor drive are not illustrated, but it will be apparent that a housing such as housing 40 can enclose varying magnetic field generator 60. A local or a remote motor drive is coupled to a drive shaft 64 to rotate a disk 62 comprising the varying magnetic field generator in either direction about an axis that extends along the longitudinal axis of drive shaft 64. Embedded within disk 62 are two sets of permanent magnets 66 and 68; the north pole face of one of these permanent magnets and the south pole face of the other permanent magnets are generally flush with the lower surface of disk 62. A flux linkage bar 70 extends between the south and north pole faces of permanent magnets 66 (within disk 62), while a flux linkage bar 72 extends between the north and the south pole faces of permanent magnets 68 (within disk 62). The relationship of the permanent magnets and flux linkage bars are best illustrated in FIG. 3B.

Rotation of disk 62 about its central axis in either direction varies the magnetic field experienced at implanted receiver coil 30 (shown in FIG. 1) and alternately changes the polarity of the field as the different permanent magnets rotate to positions adjacent to the pole faces of the implanted receiver coil. The varying magnetic field that is thus produced by rotation of disk 62 induces a generally corresponding varying electrical current in the implanted receiver coil that is usable to energize implanted medical device 34 (also shown in FIG. 1). The speed at which disk 62 rotates changes the frequency of the induced electrical current and also varies the average magnitude of the electrical current induced in the receiver coil. It is contemplated that disk 62 can be rotated at a desired rate so that the frequency of the induced current is within the range from less than 10 Hz to more than 10 kHz.

It should be noted that the power transferred to the implanted receiver coil increases as the rotational speed of the varying magnetic field generator increases. Also, as the relative spacing between varying magnetic field generator 60 and the implanted receiver coil changes, the amplitude of the induced electrical current also changes, i.e., the magnitude of the induced electrical current increases as the separation decreases. While not shown in any of the Figures, it will be apparent that the elevation of rotating disk 62 above the implanted receiver coil can be readily changed to modify the respective separation between the two devices and thereby selectively determine the maximum current induced in the implanted receiver coil—all other parameters such as rotational speed remaining constant.

FIGS. 3C–3G show further embodiments of the varying magnetic field generator of the type illustrated in FIGS. 3A and 3B. The disk configuration for the varying magnetic field generator illustrated in these Figures was first used to confirm the effectiveness of the present invention. In FIG. 3C, a disk 62' is shown without any permanent magnets. In an embodiment 60' shown in FIG. 3D, only two permanent magnets 75 and 76 are inserted within disk 62'. Other cavities 74 in disk 62' do not contain permanent magnets. Permanent magnet 75 is positioned within disk 62' with its north pole face facing downwardly, flush with the lower surface of the disk, while permanent magnet 76 is positioned with its south face facing downwardly, flush with the lower surface of the disk. The opposite pole faces of each of permanent magnets 75 and 76 are directed upwardly, and the longitudinal axes of the permanent magnets are generally aligned with the axis of drive shaft 64.

To test the efficacy of the embodiments shown in FIGS. 3C–3G, drive shaft 64 was simply chucked in a drill press (not shown) and rotated so that the lower surface of the disk in which the permanent magnets are embedded passed immediately above a receiver coil (generally like implanted receiver coil 132—shown in FIG. 2). Using only one permanent magnet 75 and one permanent magnet 76 as shown in FIG. 3D, the magnetic field intensity waveforms illustrated in the graph of FIG. 3D' were produced, which include positive pulses 78 and negative pulses 80.

When two permanent magnets 75 and two permanent magnets 76 were disposed opposite each other as shown in FIG. 3E, rotation of a disk 62" induced magnetic field intensity waveforms comprising two positive pulses 82 followed by two negative pulses 84 in repetitive sequence, as shown in FIG. 3E'. Alternating permanent magnets 75 and 76 in each of the cavities formed in a disk 62''' to produce a varying magnetic flux generator 60''' as shown in FIG. 3F, produced higher frequency magnetic field intensity waveforms, including positive pulses 86 and negative pulses 85, which are more sinusoidal, as indicated in FIG. 3F'. In the embodiment of varying magnetic field generator 60'''', shown in FIG. 3G, three permanent magnets 75 are disposed adjacent each other with their north pole faces flush with the lower surface of a disk 62'''', while three permanent magnets 76 have the south pole face flush with the lower surface of the disk. Rotation of disk 62'''' produced the magnetic field intensity waveforms shown in FIG. 3G', which include three positive pulses 88 followed by three negative pulses 90, in repetitive fashion.

In FIG. 3H, a disk 87 includes two generally arcuate shaped permanent magnets 89 and 91 disposed adjacent radially opposite sides of the disk, with the north pole of permanent magnet 89 and the south pole of permanent magnet 91 flush with the lower surface of the disk. A flux linkage bar 93 extends across the disk, over the opposite poles of the two permanent magnets. Due to the arcuate shape of the permanent magnets, they extend over a larger portion of the rotational arc of disk 87, causing generally sinusoidal magnetic field intensity waveforms 95 and 99 to be magnetically induced in the implanted receiver coil, generally as shown in FIG. 3H'.

At relatively slow rotational speeds, the rotation of one or more very strong permanent magnets directly above an implanted receiver coil may apply sufficient torque to the implanted receiver coil to cause the implanted receiver coil to move back and forth slightly. However, any movement or vibration of the implanted receiver coil due to such torque will be substantially eliminated by fastening the implanted receiver coil to adjacent bone structure. Furthermore, if the rotational speed of the varying magnetic field generator is sufficiently high, the effects of any torque applied to the implanted receiver coil will be almost imperceptible.

In FIGS. 4A and 4B, an external power head 92 is illustrated that eliminates virtually all torque on the implanted receiver coil. In this embodiment, a permanent magnet 94 is coupled through a connection 102 to a flexible cable 100, which turns within a flexible drive shaft 97. Flexible cable 100 is connected to a remote electrical drive motor (not shown in this Figure) that applies a rotational driving force to the flexible drive shaft, which rotates within a bearing 96 that is supported in a cylindrical shaped housing 104 of external power head 92. Cylindrical shaped housing 104 is fabricated of a plastic polymer that does not block or shunt magnetic flux and which does not support eddy currents. Inside cylindrical shaped housing 104, at diametrically opposite sides of the housing, are disposed two vertically aligned flux linkage blocks 98. As permanent magnet 94 rotates, its north and south poles pass adjacent to the top inwardly facing surfaces of flux linkage blocks 98, as shown clearly in FIG. 4B. The magnetic flux produced by permanent magnet 94 is then conveyed through the flux linkage blocks and coupled into underlying implanted receiver coil 132. External power head 92 is disposed on the outer surface of tissue interface 28, with the lower ends of the flux linkage blocks disposed opposite pole faces 136 of the receiver coil implanted inside the patient's body. Since permanent magnet 94 rotates in a plane that is substantially spaced apart from the bottom of cylindrical shaped housing 104, the permanent magnet applies substantially less attraction to the underlying implanted receiver coil than would be the case if the permanent magnet were rotating in a plane closer to the implanted receiver, e.g., immediately adjacent to the bottom of the cylindrical shaped housing. Furthermore, flux linkage blocks 98 tend to concentrate the magnetic flux produced by the rotating permanent magnet in a vertical direction, minimizing any horizontal component of the magnetic flux, so that little rotational force is experienced by adjacent core faces 136 of implanted receiver coil 132.

Referring now to FIG. 5, an external power head 110 is disclosed. In external power head 110, two cylindrical permanent magnets 124 are provided, each of which rotate around shafts 130 that extend through their central axis. Alternatively, more conventional bar shaped permanent magnets mounted in a plastic polymer cylinder can be used. Mechanical link bars 118 are attached to each of the permanent magnets at pivot points 122 and extend to a common pivot point 120 on a rotating driven wheel 114 that is disposed midway between the two permanent magnets. Driven wheel 114 is rotated by a drive shaft 116 that is connected to an electrical drive motor (not shown) disposed either within external power head 110, or alternatively, at a more remote location, as discussed above. Since pivot point 120 is offset from drive shaft 116, i.e., offset from the center of the driven wheel 114, movement of pivot point 120 due to rotation of the driven wheel is translated by mechanical link bars 118 into a corresponding rotational force applied to pivot points 122 that causes permanent magnets 124 to rotate about their shafts 130. As corresponding north and south poles on permanent magnets 124 move to positions immediately adjacent a curved flux linkage bar 126, the opposite poles of the permanent magnets are disposed adjacent vertically aligned flux linkage bars 128. The lower ends of the flux linkage bars are disposed adjacent the bottom of external power head 110, spaced apart and directly opposite core faces 136 of a core 134 comprising implanted receiver coil 132. This core is fabricated of a metal or alloy having a relatively high magnetic permeability. Coiled about core 134 are a plurality of turns 138 of an electrical conductor, the ends of which comprise a lead 140, which extends to the implanted medical device that receives electrical energy from implanted receiver coil 132. The varying magnetic flux applied to implanted receiver coil 132 induces a corresponding varying electrical current to flow through turns 138 and through lead 140.

Another embodiment for an external power head 150 is illustrated in FIG. 6A. In this embodiment, a driven wheel 152, fabricated of a plastic polymer or other suitable non-magnetic material bonded to a pair of permanent magnets 154, is rotated by a motor drive 162. Magnetic flux from permanent magnets 154 is coupled through a horizontally extending flux linkage bar 158 disposed above the driven wheel to a follower wheel 156, which also includes a pair of permanent magnets 154 bonded together with their respective north and south pole faces facing each other, separated by a flux linking section 157, as shown in FIG. 6B. (The structure of driven wheel 152 and follower wheel 156 is identical.) Rotation of driven wheel 152 causes a varying magnetic field polarity to be experienced by permanent magnets 154 on follower wheel 156 and the interaction with this magnetic field rotates the follower wheel generally in lock step with the rotation of driven wheel 152. As a consequence, magnetic flux from the pairs of permanent magnets 154 on the driven wheel and follower wheel couple into implanted receiver coil 132, inducing an electrical current to flow in turns 138 for use in energizing the implanted device.

The embodiments of external power heads discussed thus far have all included permanent magnets that rotate. In FIG. 7, an external power head 170 is illustrated that includes a flux linkage bar 174 mounted to a shaft 176. Shaft 176 reciprocatively rotates back and forth, causing permanent magnets 172 to pass back and forth above core faces 136 of implanted receiver coil 132. As the magnetic flux produced by the permanent magnets and experienced by implanted receiver coil 132 periodically changes due to the reciprocating movement of the permanent magnets back and forth above the pole faces of the implanted receiver coil, an electrical current is induced to flow within the turns of the conductor wrapped around core 134 (not separately shown in FIG. 7), to energize the implanted device (also not shown in this Figure).

Instead of being rotatably reciprocated back and forth, the permanent magnets can be driven to move back and forth in a linear fashion, as in the embodiment of an external power head 180 illustrated in FIG. 8. In this embodiment, a flux shunt bar 186 is disposed above three vertically aligned and spaced-apart permanent magnets 182 and extends over the respective north and south poles of two of the permanent magnets. The upwardly facing poles of permanent magnets 182 are respectively south, north, and south (or each can be of opposite polarity), in the order in which they are attached to a moving plate 184 that is driven back and forth. The spacing between permanent magnets 182 is such that at the two extreme linear positions of reciprocating plate 184, the poles of two of the permanent magnets disposed immediately above core faces 136 on implanted receiver coil 132 are opposite in polarity. Linear reciprocating movement of reciprocating plate 184 is provided by an appropriate drive mechanism (not shown), receiving its motive power from an electrical motor drive (also not shown), which is disposed either locally with the external power head, or remotely and coupled to the external power head by a drive shaft.

In FIG. 9, an embodiment of a power head 190 is illustrated that includes provision for selectively electrically controlling the strength of the magnetic field coupled to implanted receiver coil 132. In this embodiment, instead of varying the separation between rotating permanent magnets 192 and implanted receiver coil 132, an electrical conductor 194 is coiled around each of permanent magnets 192 and coupled to a variable current power supply (not shown) that provides a direct current (DC) flowing through conductor 194. Since permanent magnets 192 are rotating, being driven by an electrical motor drive (also not shown in FIG. 9), conductor 194 must be coupled to the variable power supply using slip rings, brushes, a rotary transformer, or other suitable mechanism, as is commonly used for coupling power to a conductor on a rotating armature of an electric motor. The DC current passing through conductor 194 can either assist or oppose the magnetic field produced by permanent magnets 192, thereby selectively varying the strength of the magnetic field experienced by implanted receiver coil 132 to control the magnitude of the electrical current that the implanted receiver coil supplies to the implanted device.

Another way to periodically vary the magnetic field experienced by implanted receiver coil 132 is to periodically change the efficiency with which the magnetic flux produced by permanent magnets couples to the implanted receiver coil. FIG. 10 illustrates one technique for varying the magnetic flux linkage between two permanent magnets 202 in an external power head 200 and the implanted receiver coil. Permanent magnets 202 are stationary. A motor drive (not shown in this Figure) drivingly rotates two disks 204 that are disposed behind each of the fixed permanent magnets. Tabs 206 extend outwardly from the facing surfaces of disks 204 a distance equal to a little more than the thickness of permanent magnets 202 (measured in a direction normal to the plane of the paper in the Figure). Tabs 206 and disks 204 are fabricated of a metal or an alloy having a high magnetic permeability that provides enhanced flux linkage when disposed adjacent the poles of permanent magnets 202. A flux shunt bar 186 that is also fabricated of a material having a high magnetic permeability extends above permanent magnets 202, but is spaced sufficiently apart from the upwardly facing poles of the permanent magnets to provide clearance for tabs 206 to pass between the flux shunt bar and the poles of permanent magnets 202. As tabs 206 rotate between the upper poles of permanent magnets 202 and the undersurface of flux shunt bar 186, and between the lower poles of the permanent magnets and core faces 136 of implanted receiver coil 132 (as shown by the dash lines that illustrate the tabs in phantom view), the flux linkage between permanent magnets 202 and core 134 greatly decreases so that substantially less magnetic field strength is experienced by the implanted receiver coil. The magnetic flux produced by the permanent magnets is shunted through disks 204, with little of the magnetic flux flowing between the poles of the permanent magnets passing through the implanted receiver coil. However, as disks 204 continue to rotate so that tabs 206 move to the positions shown by the solid lines in FIG. 10, the flux linkage between permanent magnets 202 and implanted receiver coil 132 approaches a maximum. Thus, rotation of disks 204 causes core 134 to experience a varying magnetic field that induces an electrical current to flow within the conductor comprising turns 138.

As shown in FIG. 11, a further embodiment of the varying magnetic field generator includes a flux linkage bar 225 and a rotating flux linkage bar 214 connected to a drive shaft 212 that rotates the flux shunt in a plane below the pole faces of permanent magnets 202. Fixed flux linkage bar 225 and rotating flux linkage bar 214 are both fabricated of a metal or alloy characterized by its ability to substantially shunt magnetic flux. When rotating flux linkage bar 214 is in the position represented by the phantom view (dash lines), i.e., in a position at 90° to the longitudinal axis of fixed flux linkage bar 225, the flux linkage between the permanent magnets and the implanted receiver coil (not shown in this Figure) is at a maximum, and when the rotating flux shunt is in the position shown (by the solid lines) in FIG. 11, the magnetic flux produced by the permanent magnets is substantially shunted between them through the rotating flux shunt. Due to the resulting periodically varying magnetic flux coupling, an electrical current is induced in the implanted receiver coil. FIG. 11' illustrates magnetic field pulses 218 that appear at the implanted receiver coil as the flux shunt rotates.

A desirable feature of the embodiments shown in both FIGS. 10 and 11 is that when the devices are de-energized, leaving the magnet flux shunted between the poles of the permanent magnets, very little magnetic field produced by the permanent magnets escapes outside the housing (not shown). The rotating flux shunts thus serve to "turn off" the external magnetic field by shunting it between the poles of the permanent magnets.

FIG. 12 illustrates a rotating ring external power head 220 that is intended to induce an electrical current to flow within an implanted receiver coil 227 that is disposed within the head, neck, leg, or arm of a patient encompassed by the external power head. In the example shown in FIG. 12, the rotating ring external power head has been slipped around a leg 222 and positioned generally adjacent implanted receiver coil 227. Although other designs and shapes of the implanted receiver coil may be employed, implanted receiver coil 227 is configured as a short core 229 about which a conductor 231 is coiled. The conductor is connected to an implanted device (not shown), to provide electrical power used to energize the device or to charge an energy storage component (battery or capacitor—neither shown). It should be noted that implanted receiver coil 227 can be used with the other embodiments of the present invention and is preferably disposed so that core 229 is generally facing toward the dermal surface so that one end of the core will intercept the varying magnetic flux produced by any of the various external power heads disclosed herein. A plurality of permanent magnets 226 are mounted to an inner ring 228 and are oriented so that a longitudinal axis of each of the permanent magnets is radially aligned relative to the rotating ring external power head. Inner ring 228 extends circumferentially around the rotating ring external power head and is movably supported between fixed sides 224 on bearings (not shown) that enable it and the plurality of permanent magnets to move around the center of the rotating ring external power head. The alternating north and south poles of successive permanent magnets 226 thus pass adjacent to the end of core 229 of implanted receiver coil 227 as the inner ring rotates, causing a varying magnetic flux to be experienced by the implanted receiver coil. A motor 242, coupled to a power supply/control (not shown), is attached to one side 224 of the rotating ring external power head. The motor drivingly rotates a shaft 246 on which is mounted a friction drive wheel 244. The friction drive wheel engages the inner ring, providing the driving force that rotates the inner ring and the permanent magnets about the center of the rotating ring external power head, moving them past implanted receiver coil 227. It will be apparent that different diameter rotating ring external power heads can be used as appropriate for the diameter of the portion of the body that is to be encompassed by the device. Also, it will be apparent that other drive mechanisms can be used to provide the motive force for moving the plurality of permanent magnets relative to the implanted receiver coil.

When the electric motor that is the prime mover for any of the external power heads described above is initially energized to provide the rotational, pivotal, or linear reciprocating motion, the motor experiences a starting torque (that resists its rotation) because of the magnetic attraction between permanent magnets and any flux linkage bar included in the external power head, and the implanted receiver coil. FIG. 13 illustrates an embodiment for a power head 230 that minimizes the starting torque experienced by the electrical motor. In this embodiment, a drive shaft 232 is coupled to the local or remotely disposed electrical motor drive. The lower end of drive shaft 232 is connected to a horizontally extending cylindrical tube 236. Permanent magnets 238 are supported within cylindrical tube 236 and are able to move radially inward or outward relative to the longitudinal axis of drive shaft 232. The permanent magnets are coupled to a helically coiled spring 234 that extends between the permanent magnets, within the center of cylindrical tube 236 and applies a force that tends to draw the permanent magnets radially inward, away from the upper ends of flux linkage rods 240. When the motor drive that is coupled to drive shaft 232 is de-energized, permanent magnets 238 are thus drawn toward each other, minimizing the torque required to begin rotating cylindrical tube 236. However, when a motor drive 233 begins to rotate drive shaft 232, the centrifugal force created by rotation of cylindrical tube overcomes the force of helical spring 234, causing permanent magnets 238 to slide radially outward, away from the central axis of drive shaft 232, until the permanent magnets reach stops (not shown) that limit their radial travel so that their poles are closely spaced apart from flux linkage rods 240. Magnetic flux linkage to implanted receiver coil 132 is then achieved.

In FIGS. 14A and 14B, two alternative techniques are shown for minimizing startup torque. However, a further advantage is provided by these alternatives, since they enable the magnitude of the current produced by the implanted receiver coil to be controlled by varying the spacing between permanent magnets 238 and flux linkage rods 240 when the permanent magnets are rotating past the flux linkage rods. Specifically, as the spacing between the permanent magnets and flux linkage rods is increased, both the coupling of magnetic flux into the implanted receiver coil and the magnitude of the electrical current induced in the implanted receiver coil are reduced.

FIG. 14A shows an external power head 248 in which drive shaft 232 rotates a ring permanent magnet 250 with a cylindrical tube 236' and permanent magnets 238 about the longitudinal axis of the drive shaft. A solenoid coil 252 is wound around drive shaft 232 and is coupled to an electrical current source/control 254. Electrical current provided by the electrical current source/control is varied to provide a controlled magnetic force that causes ring permanent magnet 250 to move upwardly along drive shaft 232 by a controlled amount. Mechanical links 256 are pivotally connected to the ring permanent magnet and extend through a slot 260 in the cylindrical tube to couple with pivot connections 258 on the facing poles of permanent magnets 238. As the ring permanent magnet is drawn up drive shaft 232, permanent magnets 238 are drawn radially inward toward each other, reducing the magnetic flux coupled into the implanted receiver coil (not shown in this drawing) through flux linkage rods 240. Also, when the drive shaft is initially rotated, the permanent magnets are drawn relatively closer still to each other, thereby minimizing the startup torque by reducing the attraction between the permanent magnets and the flux linkage rods.

In FIG. 14B, an alternative external power head 262 is shown that achieves much the same result as external power head 248. However, in this embodiment, a swash plate 264 is connected to pivotal connectors 258 through mechanical links 256. Swash plate 264, cylindrical tube 236' and permanent magnets 238 are rotated by drive shaft 232. However, in this embodiment, bearing rollers 266 act on opposing surfaces of swash plate 264 to control its position along drive shaft 232 as the drive shaft rotates. The bearing rollers are mounted on a bracket 268 that is connected to a piston rod 270.

The position of the piston rod and thus, the position of the bearing rollers and swash plate is adjusted by actuating a pressurized fluid cylinder 272 by applying pressurized hydraulic or pneumatic fluid through lines 274. The pressurized fluid is applied to drive the piston rod up or down and thereby move swash plate 264 up or down along drive shaft 232. As the swash plate moves up along drive shaft 232, it pulls permanent magnets 238 radially inward toward each other. In the fully retracted positions, permanent magnets are only weakly linked through flux linkage rods 240 and the startup torque necessary to begin rotating drive shaft 232 is minimal. As the swash plate is moved downwardly along drive shaft 232, the permanent magnets are forced outwardly, increasing the magnetic flux coupling between the rotating permanent magnets and the implanted receiver coil. Accordingly, the magnitude of the electrical current induced in the implanted receiver coil will be increased. It will be apparent that using either of the embodiments of the external power head shown in FIGS. 14A or 14B, the magnitude of the electrical current induced in the implanted receiver coil is readily controlled.

Finally, FIG. 15 illustrates an external power head 280 the includes a housing 282 in which a divider 286 extends between a lower compartment 284 and an upper, generally dome-shaped, compartment 288. In the lower compartment 284 are disposed a motor 290 capable of turning a drive shaft 292 at a relatively high speed, e.g., to more than 20,000 rpm. Mounted on drive shaft 292 is a rod-shaped permanent magnet 294. Motor 290 is energized with an electrical current controlled by a motor speed control circuit 296 that is disposed in upper compartment 288. The motor speed control circuit is coupled to the motor through a lead 298 and is energized with electrical current supplied from a battery pack 304 to which the motor speed control circuit is connected. A speed control knob 306 extends above the housing of tile external power head and is rotatable by the user to turn the device on or off and to vary the speed at which motor 290 rotates. Speed control knob 306 actuates a variable resistor 300, which is mounted just inside the top of the upper compartment, using a pair of threaded nuts 308. The variable resistor is connected to the motor speed control circuit through leads 302.

As illustrated in the Figure, external power head 280 is intended to be disposed on tissue interface 28, so that permanent magnet 294 is generally adjacent-an implanted air core receiver coil 276 (or other implanted receiver coil). The term "air core" simply indicates that a ferrous alloy or other material having a relatively high magnetic permeability is not used as a core for this particular implanted receiver coil. Instead, this embodiment of an implanted receiver coil comprises a relatively flat or pancake-shaped coil of a conductor that is preferably coated with (or embedded in) a biocompatible polymer to protect it from exposure to bodily fluids. Leads from the implanted air core receiver coil supply electrical current to an implanted device, and the electrical current is induced to flow in the coil by the varying magnetic flux produced as permanent magnet 294 is rotated by the motor. Due to the speed at which permanent magnet 294 rotates, a relatively efficient magnetic flux coupling exists between the permanent magnet and the implanted air core receiver coil.

By varying the speed at which the permanent magnet rotates, it is possible to control the magnitude of the current induced in the implanted air core receiver coil. As the speed at which the permanent magnet rotates is increased, the magnitude of the electrical current produced by the implanted air core receiver coil increases. It is contemplated that speed control knob 306 may be indexed to marks (not shown) that are provided on the exterior of housing 282 to indicate a range of electrical current for different settings of the speed control knob. Of course, the magnetic flux linkage can also be controlled by varying the separation between the external power head and the implanted air core receiver coil.

Although the present invention has been described in connection with the preferred form of practicing it, those of ordinary skill in the art will understand that many modifications can be made thereto within the scope of the claims that follow. Accordingly, it is not intended that the scope of the invention in any way be limited by the above description, but instead be determined entirely by reference to the claims that follow.

The invention in which an exclusive right is claimed is defined by the following:

1. A method for generating a varying magnetic field to couple energy to an implanted receiver coil, comprising the steps of:
   (a) generating a magnetic field;
   (b) coupling a driving force to an element so that the element is movable; and
   (c) moving the element with the driving force in a reciprocating motion to vary the magnetic field coupled to the implanted receiver coil, variation of said magnetic field coupled to the implanted receiver coil causing a varying electrical current to be induced in the implanted receiver coil.

2. The method of claim 1, wherein a source of the driving force is disposed remote from where the magnetic field is generated and is coupled to the element through a driven shaft.

3. The method of claim 1, wherein said element is moved sufficiently fast to magnetically couple with an air core implanted receiver coil.

4. The method of claim 1, wherein the magnetic field is generated with at least one permanent magnet.

5. The method of claim 4, wherein the permanent magnet comprises a rare earth alloy.

6. The external transmitter of claim 5, further comprising the step of providing an electrical current flow through a plurality of turns of a conductor wound around said at least one permanent magnet to selectively adjust a maximum value of the magnetic field produced by said at least one permanent magnet, said electrical current producing a magnetic field that either increases or reduces the magnetic field generated said at least one permanent magnet support is rotated, a separation of said plurality of permanent magnets being controlled to adjust the magnetic field coupled to the implanted receiver coil.

7. The method of claim 4, wherein the element that is moved comprises said at least one permanent magnet.

8. The method of claim 7, further comprising the step of enhancing magnetic flux linkage between magnetic poles of the permanent magnet and the implanted receiver coil by providing a flux linkage bar for coupling a magnetic field from a pole of the permanent magnet into the implanted receiver coil, enabling the permanent magnet to be displaced from the implanted receiver coil.

9. The method of claim 1, further comprising the step of selectively varying a maximum magnetic field intensity coupled with the implanted receiver coil.

10. The method of claim 9, wherein the step of selectively varying the maximum magnetic field intensity comprises the step of positioning the element relative to the implanted receiver coil to control the magnetic field coupled to the implanted receiver coil.

11. The method of claim 9, wherein the step of selectively varying the maximum magnetic field intensity comprises the step of changing a speed with which the element moves.

12. Tile method of claim 1, wherein the magnetic field is generated with a plurality of permanent magnets.

13. The method of claim 12, wherein the plurality of permanent magnets are fixed relative to the support, and wherein the step of moving the element comprises the step of intermittently passing a flux shunt member adjacent pole faces of the plurality of permanent magnets so as to provide a magnetic flux shunt path between the pole faces of the plurality of permanent magnets, to produce the varying magnetic field.

14. A method for generating a varying magnetic field to couple energy to a receiver coil implanted in an extremity of a patient, comprising the steps of:
   (a) generating a magnetic field with a plurality of magnets that are movable about the extremity of the patient;
   (b) coupling a driving force to the plurality of magnets; and
   (c) rotating the plurality of magnets around the extremity, thereby varying the magnetic field coupled to the receiver coil, variation of said magnetic field coupled to the receiver coil causing a varying electrical current to be induced in the implanted receiver coil.

15. A method for generating a varying magnetic field to couple energy to an implanted receiver coil, comprising the steps of:
   (a) generating a magnetic field;
   (b) coupling a driving force to an element comprising at least one magnet so that the element is movable;
   (c) moving the element with the driving force to vary the magnetic field coupled to the implanted receiver coil, variation of said magnetic field coupled to the implanted receiver coil causing a varying electrical current to be induced in the implanted receiver coil; and
   (d) enhancing magnetic flux linkage between magnetic poles of said at least one permanent magnet and the implanted receiver coil by providing a flux linkage bar that couples a magnetic field from a pole of said at least one permanent magnet into the implanted receiver coil.

* * * * *

UNITED STATES PATENT AND TRADEMARK OFFICE
CERTIFICATE OF CORRECTION

PATENT NO. : 6,092,531
DATED : July 25, 2000
INVENTOR(S) : Chen et al.

Page 1 of 1

It is certified that error appears in the above-identified patent and that said Letters Patent is hereby corrected as shown below:

<u>Title page,</u>
Section [56], U.S. Patent Documents, 15th Reference, "4,461,302  7/1984  Philipps et al." should read -- 4,461,302  7/1984  Phillipps et al. --

<u>Column 2,</u>
Line 6, "How" should read -- flow --

<u>Column 6,</u>
Line 60, "arc" should read -- are --

<u>Column 14,</u>
Line 45, "tile" should read -- the --

<u>Column 15, claim 6,</u>
Line 57, after "magnet" delete "support is rotated, a separation of said plurality of permanent magnets being controlled to adjust the magnetic field coupled to the implanted receiver coil"

<u>Column 16, claim 12,</u>
Line 20, "Tile" should read -- The --

Signed and Sealed this

Eleventh Day of September, 2001

Attest:

*Nicholas P. Godici*

NICHOLAS P. GODICI
*Acting Director of the United States Patent and Trademark Office*

*Attesting Officer*